(12) United States Patent
Nguyen et al.

(10) Patent No.: US 9,855,199 B2
(45) Date of Patent: *Jan. 2, 2018

(54) COSMETIC BASE COMPOSITION AND ITS USE

(71) Applicant: Coty Germany GmbH, Mainz (DE)

(72) Inventors: Lethu Nguyen, Colonia, NJ (US); Salvatore J. Barone, Staten Island, NY (US); Ralph Macchio, Sparta, NJ (US)

(73) Assignee: Coty Germany GmbH, Mainz (DE)

( * ) Notice: Subject to any disclaimer, the term of this patent is extended or adjusted under 35 U.S.C. 154(b) by 0 days.

This patent is subject to a terminal disclaimer.

(21) Appl. No.: 14/806,376

(22) Filed: Jul. 22, 2015

(65) Prior Publication Data

US 2015/0320653 A1  Nov. 12, 2015

Related U.S. Application Data

(63) Continuation of application No. 13/255,709, filed as application No. PCT/EP2010/052985 on Mar. 9, 2010, now Pat. No. 9,119,785.

(30) Foreign Application Priority Data

Mar. 9, 2009 (EP) .................................... 09154667

(51) Int. Cl.
*A61K 8/14* (2006.01)
*A61K 8/73* (2006.01)
*A61Q 1/02* (2006.01)
*A61Q 19/00* (2006.01)

(52) U.S. Cl.
CPC ............... *A61K 8/14* (2013.01); *A61K 8/731* (2013.01); *A61Q 1/02* (2013.01); *A61Q 19/00* (2013.01); *A61K 2800/30* (2013.01); *A61K 2800/33* (2013.01); *A61K 2800/34* (2013.01); *A61K 2800/48* (2013.01)

(58) Field of Classification Search
None
See application file for complete search history.

(56) References Cited

U.S. PATENT DOCUMENTS

| | | | |
|---|---|---|---|
| 5,086,077 A | 2/1992 | Obara et al. | |
| 5,643,583 A * | 7/1997 | Voultoury | A61K 8/14 424/401 |
| 5,683,740 A | 11/1997 | Voultoury et al. | |
| 7,902,134 B1 * | 3/2011 | Lutrario | A61K 8/14 510/130 |
| 9,119,785 B2 | 9/2015 | Nguyen et al. | |
| 2008/0241082 A1 | 10/2008 | Guth et al. | |
| 2009/0280149 A1 | 11/2009 | Tajima et al. | |
| 2010/0047202 A1 * | 2/2010 | Goddinger | A61K 8/731 424/70.12 |
| 2010/0068162 A1 * | 3/2010 | Greenberg | A61K 8/31 424/59 |
| 2011/0110989 A1 | 5/2011 | Simonnet et al. | |

FOREIGN PATENT DOCUMENTS

| | | | |
|---|---|---|---|
| CN | 1116903 A | 2/1996 | |
| JP | 2007112787 | 5/2007 | |
| JP | 2008031044 | 2/2008 | |
| WO | 98/53698 | 12/1998 | |
| WO | 2005/030169 | 4/2005 | |
| WO | 2005/097059 | 10/2005 | |
| WO | 2007/102052 | 9/2007 | |
| WO | 2008/001902 | 1/2008 | |
| WO | WO 2008077683 A2 * | 7/2008 | ............. A61K 8/731 |
| WO | WO-2010/103008 | 9/2010 | |

OTHER PUBLICATIONS

Database Caplus, Chemical Abstracts Service (Feb. 14, 2008) Kao Corp: XP002545591.
Database Caplus, Chemical Abstracts Service (May 10, 2007) Shiseido Co., Ltd.: XP002545592.
Written Opinion of the International Searching Authority for International Application No. PCT/EP2010/052985, opinion completed Jun. 1, 2010.
Nohata, et al., "Structural studies of a neutral polysaccharide produced by Alcaligenes lactus," Carbohydrate Research, 1996, vol. 293, pp. 213-222
Guth, et al., "Oleosomes: natural, self-emulsifying systems," Cosmetics & Toiletries, 2006, vol. 121, No. 1, pp. 49-57.
"Sangelose" by Uniglobe Kisco, Inc. 2009, http://www.uniglobe-kisco.com/sangelose/html.
"Riken Natural Tocopherol Products" by Riken Vitamin, 2002, http://www.rikenvitamin.jp/int/tocopherol/products.html.
Chinese Application Serial No. 201510459776.4, Office Action dated May 27, 2017, With English Translation, 14 pgs.

* cited by examiner

*Primary Examiner* — Ileana Popa
*Assistant Examiner* — Alissa Prosser
(74) *Attorney, Agent, or Firm* — Schwegman Lundberg & Woessner, P.A.

(57) ABSTRACT

The present invention relates to a cosmetic basic composition comprising hydroxypropylmethylcellulose (HPMC) modified with C15-C20 alkyl ether groups as thickener, Oleosomes and water, wherein the Oleosomes comprise at least one cosmetically active substance. The invention also relates to the use of the cosmetic basic composition in products of decorative cosmetics, personal care cosmetics and/or skin protection cosmetics.

4 Claims, No Drawings

COSMETIC BASE COMPOSITION AND ITS USE

CROSS-REFERENCE TO RELATED APPLICATIONS

This application is a continuation application of U.S. patent application Ser. No. 13/255,709, filed Nov. 18, 2011, which is a §371 national stage entry of International Application No. PCT/EP2010/052985, filed Mar. 9, 2010, which claims priority to European Patent Application No. EP 09154667.1, filed Mar. 9, 2009, the entire contents of which are incorporated herein by reference.

FIELD OF THE INVENTION

The present invention relates to a cosmetic basic composition comprising a hydrophobic hydroxypropylmethylcellulose (HPMC) as thickener which is a HPMC modified with C15-C20 alkyl ether groups, Oleosomes and water, wherein the Oleosomes comprise at least one cosmetically active substance. The invention also relates to the use of the cosmetic basic composition in products of decorative cosmetics or personal care cosmetics, preferably skin care or skin protection cosmetics.

BACKGROUND OF THE INVENTION

Oleosomes also known as oil bodies, lipid bodies or spherosomes are vegetable discrete oil microspheres which occur naturally in the cells of seeds of oilseed crops and in which plants store energy in the form of oil. The stored oil is protected from oxidation and deterioration by the presence of antioxidants.

Natural Oleosomes consist of an outer coat of phospholipids and proteins (oleosines) and an internal liquid, semi-solid, or low melting solid collection of triglycerides associated with the individual plant seed. Thus, the water insoluble oil fraction in plant cells is stored in discrete subcellular structures. From a structural point of view Oleosomes are considered to be a triacylglyceride matrix encapsulated by a monolayer of phospholipids in which Oleosome proteins, in particular the oleosine, are embedded.

Oleosomes are known to be used in industrial processes. For example WO 98/53698 discloses a method for preparing emulsion formulations comprising Oleosomes preferably extracted from plant cells. The emulsions can be used in food and feed products, pharmaceutical products, personal care products and industrial products. WO 2005/097059 A1 describes a preparation process of cosmetic oil-in-water emulsions with oleosomes which process comprises no heating step.

For personal care products and products of decorative cosmetics the consumers expect easy application, comfortable skin feeling and long wearing properties. An initial or freshly applied look should be provided over several hours. However, the mobility of the applied products often allows the product to migrate and concentrate into fine lines or wrinkles resulting in an undesirable non-uniform look.

Personal care products and products of decorative cosmetics, especially colored products should also provide a high transfer resistance so that the applied products remain onto the skin and do not transfer easily to the surfaces brought into contact, such as clothes, glasses etc.

Usually film forming agents and high contents of fatty phase liquid ingredients, such as silicone oils or hydrocarbons and waxes are used to impart long wearing and transfer resistance to cosmetic compositions. However, a greasy and unpleasant skin feeling often results. If also high water contents should be included into the formulations in order to impart moisturizing effects to the cosmetic compositions high contents of emulsifiers are needed. However, for consumers with sensitive skin the use of skin irritating substances like silicone oils, emulsifiers and surfactants should be avoided or at least strongly reduced in cosmetic compositions.

SUMMARY OF THE INVENTION

It is the object of the present invention to provide a cosmetic basic composition which is long wearing and transfer resistant. The cosmetic basic composition of the invention should impart a comfortable skin feeling with a low or no skin irritating potential. The cosmetic basic composition should also show a pleasant texture and should be easy to apply.

It is a further object of the present invention to use said cosmetic basic composition in products of decorative cosmetics and personal care cosmetics, especially for skin care and/or skin protection.

It is another object of the present invention to provide an advantageous method of preparing said cosmetic basic composition.

The present invention provides a long wearing and transfer resistant cosmetic basic composition comprising a hydroxypropylmethylcellulose $C_{15}$-$C_{20}$ alkyl ether thickener, Oleosomes and water, wherein the Oleosomes comprise at least one cosmetically active substance. The cosmetic basic composition of the invention is self-leveling and shows a low skin irritation potential.

Surprisingly, the cosmetic basic composition of the invention is extremely long lasting and can be applied easily. The overall skin feeling after application is comfortable and lightweight. In addition, the cosmetic basic composition of the invention shows high transfer resistance and moisturizes and humidifies the skin. Thus, the cosmetic basic composition of the present invention provides a very special combination of advantageous properties which is not achieved by products of the state of the art.

It is also advantageous that a high water content can be formulated into the composition using the emulsifying properties of the Oleosomes without impairing the stability of the composition. Thus, synthetic emulsifiers or surfactants are not (or only in extremely small amounts) needed and hence, the cosmetic basic composition is also suitable for sensitive skin areas. Hence, the cosmetic basic composition of the invention can be used for all parts of the skin and even for highly sensitive skin, e.g. near the eyes.

It is a further advantage of the present invention that the cosmetic basic composition also meets the aesthetics requirement of the consumers. Due to self-leveling the composition surface equalizes automatically and the container containing the cosmetic basic composition appears always untouched. The self-leveling property of the cosmetic basic composition of the invention is also advantageous when the composition is applied to the skin. The texture of the composition has been considered very good and comfortable by the consumers. Advantageously, the cosmetic basic composition also shows long-term stability.

A preferred hydroxypropylmethylcellulose $C_1$-$C_{20}$ alkyl ether thickener according to the invention is hydroxypropylmethylcellulose stearoxy ether (Tradename: Sangelose). The stearyloxy group is bound via the hydroxypropoxy group to the cellulose monomer units (—OCH$_2$CH(OH)

$CH_2OC_{18}H_{37}$). According to the invention the content of the stearyloxy hydroxypropoxy group in the hydroxypropyl-methylcellulose stearoxy ether is in the range of 0.1 to 4.0 weight percent, preferably in the range of 0.1 to 2.0 weight percent, more preferred in the range of 0.3 to 0.6 weight percent based on the molecular weight of the hydroxypropyl-methylcellulose stearoxy ether.

Surprisingly, the use of the hydroxypropylmethylcellulose $C_{15}$-$C_{20}$ alkyl ether thickener is very advantageous for the cosmetic basic composition of the invention, because this HPMC derivative imparts to the composition a high viscosity even in small quantities (like 0.1-1.0, preferably 0.1-0.5 weight percent based on the total weight of the basic composition) and a thixotropic fluidity. The viscosity increases by increasing contents of stearyloxy groups of the HPMC derivative used in the invention and decreases with increasing temperature. However, only hydroxypropylmethylcellulose stearoxy ether thickeners with a content of stearyloxy groups up to 0.6 weight percent are water soluble. Thickeners with a higher content of stearyloxy groups can be solved in a mixture of water and alcohol, preferably in a mixture of water and isopropyl alcohol. If the cosmetic basic composition is formulated for sensitive skin water soluble hydroxypropylmethylcellulose $C_{15}$-$C_{20}$ alkyl ether thickeners are preferred.

DETAILED DESCRIPTION

In a preferred embodiment of the invention the hydroxypropylmethylcellulose $C_{15}$-$C_{20}$ alkyl ether thickener is hydroxypropylmethylcellulose stearoxy ether. A suitable trade product which can be used according to the invention is for example Sangelose which is available for instance from the Daido Chemical Corporation. Sangelose 90L, Sangelose 90M, Sangelose 90H, Sangelose 60L, Sangelose 60M and Sangelose 60H can be used according to the invention which all contain different contents of stearyloxy groups. According to the invention Sangelose 90L is preferred which comprises 0.3-0.6 weight percent of stearyloxy hydroxypropoxy groups, based on the MW of the hydroxypropylmethylcellulose stearoxy ether.

In a preferred embodiment of the invention the hydroxypropylmethylcellulose $C_{15}$-$C_{20}$ alkyl ether thickener is contained in an amount of 0.1 to 5 percent by weight, preferably in an amount of 0.1 to 2 percent by weight and more preferred in an amount of 0.1 to 1 percent by weight based on the total weight of the composition.

In a more preferred embodiment of the invention the HPMC $C_{15}$-$C_{20}$ alkyl ether thickener is contained in an amount of at about 0.5 percent by weight based on the total weight of the composition.

According to the invention Oleosomes are formulated into the cosmetic basic composition of the invention. Oleosomes are used as skin caring agents and vehicles for cosmetically active ingredients. According to the invention natural Oleosomes are used themselves or they additionally carry oil soluble cosmetically active substances. During application the Oleosome structure collapses and the ingredients are released to the skin. Thereby the phospholipid coat forms a lamellar structure caring and protecting the skin from the environment. Intact Oleosomes are able to emulsify the water and the oily phase of the cosmetic basic composition.

Preferably Oleosomes of plant cells, in particular of seed cells are used, more preferred the Oleosomes are natural Oleosomes of plants of the family of Asteraceae, preferably of the genus *Carthamus*, most preferred of *Carthamus Tinctorius* (safflower).

Safflower seed Oleosomes are typically 3 µm in diameter and contain usually 99% safflower oil, 1% phospholipid+Oleosin and traces of antioxidants, in particular Vitamin E. Safflower oil usually comprises 6.5% palmitic acid, 2.5% stearic acid, 11.5% oleic acid, 79% linoleic acid and 0.5% linolenic acid. Suitable safflower Oleosomes according to the invention can be obtained for example as a 70-75 wt-% in water emulsion, for instance as 75% dispersion or O/W emulsion in water (INCI name: *Carthamus Tinctorius* (Safflower) Oleosomes) or as 60% dispersion in equal parts of glycerin and water (20%/20%) (INCI name: *Carthamus Tinctorius* (Safflower) Oleosomes and Glycerin). Preferred trade products according to the invention are for example Hydresia and Hydresia G2 from Botaneco.

In one embodiment of the invention natural Oleosomes, preferably *Carthamus Tinctorius* (Safflower) Oleosomes are used for the cosmetic basic composition of the invention. These Oleosomes comprise only the ingredients which are naturally contained. The composition of the naturally included ingredients depends only on the plant from which the Oleosomes are extracted. Special compositions may be achieved by breeding or by genetic engineering of the plants.

In another embodiment of the invention the natural Oleosomes are loaded with oil soluble cosmetically active substances. Thereby the Oleosome structure is not disrupted. Several factors, such as viscosity and pH of the solution or charge, molecular weight ($M_w$) and HLB of the substances to be loaded may influence the loading procedure. Loading levels of approximately 50 percent by weight of the Oleosomes can be achieved. Preferably loaded substances are fatty alcohols, esters, amides and triglycerides with a $M_w$>3000. In a preferred embodiment of the invention the Oleosomes are loaded with cosmetically suitable skin and/or hair actives, antioxidants, UV-filter, fragrances, such as methyl salicylate, insect repellents or stem cells.

Loading may be performed by passive diffusion of the oil soluble active ingredients into the Oleosomes by penetrating the phospholipid monolayer. A suitable method of loading is described for example in WO 2005/030169 which is based on the partitioning coefficient of the oil soluble active ingredient in different solvents.

According to the invention any oil soluble active ingredient known to the skilled person can be used as the at least one cosmetically active substance contained in the Oleosomes. In a preferred embodiment the at least one cosmetically active substance contained in the Oleosomes is selected from the group consisting of cosmetically skin and/or hair actives, anti-oxidants, such as vitamins, carotinoides, glutathion, polyphenols or flavonoides, mono- or polyunsaturated fatty acids, anti-aging agents, anti-wrinkles agents, emollients, skin conditioning agents, UV-filters, fragrances, insect repellents, stem cells or mixtures thereof.

Suitable antioxidants are for instance vitamins, such as vitamin C and derivatives thereof, for instance ascorbyl acetate, ascorbyl phosphate, ascorbyl palmitate or magnesium ascorbyl phosphate, vitamin A and derivatives thereof, folic acid and derivatives thereof, vitamin E and derivatives thereof, such as tocopheryl acetate, flavones and flavonoides, amino acids, such as histidine, glycine, tyrosine, tryptophan and derivatives thereof, imidazoles, such as cis- or trans-urocanic acid and derivatives thereof, peptides, such as D,L-carnosine, D-carnosine, L-carnosine and derivatives thereof, carotenoides, such as xanthophylles and carotenes, such as α-carotene, β-carotene, lycopine, uric acid and derivatives thereof, α-hydroxy acids, such as citric acid, lactic acid, malic acid, α-hydroxy fatty acids, such as palmitic acid, phytic acid, lactoferrin, stilbenes and derivatives thereof, mannose and derivatives thereof, liponic acid and derivatives thereof, such as dihydrolipoic acid, ferulic acid and derivatives thereof, thiols, such as glutathion, cysteine, cystine and esters thereof, folic acid and derivatives thereof or polyphenols and derivatives thereof.

Suitable monounsaturated fatty acids according to the invention are for instance palmitoleic acid, cis-vaccenic acid, oleic acid, eicosenoic acid, erucic acid and nervonic acid. Suitable polyunsaturated fatty acids are for instance α-linolenic acid, stearidonic acid, eicosatrienoic acid, eicosatetraenoic acid, eicosapentaenoic acid, docosapentaenoic acid, docosahexaenoic acid, tetracosapentaenoic acid, nisinic acid, linoleic acid, γ-linolenic acid, eicosadienoic acid, dihomo-γ-linolenic acid, arachidonic acid, docosadienoic acid, adrenic acid, docosapentaenoic acid, calendic acid and mead acid.

Anti-oxidants are also the most powerful anti-aging and anti-wrinkles agents. According to the invention further all substances which tight the skin or accelerate healing, repairing or renewing processes can be included as anti-aging and anti-wrinkles agents into the cosmetic basic composition of the invention. Suitable examples are plant extracts, such as seaweed extract, coenzymes and enzymes, provitamins, trace elements, hyaluronic acid, proteins and peptides, in particular proteins of the extracellular matrix or peeling agents. A preferred anti-aging agent according to the invention is a mixture comprising Glycerin, water, Butylene Glycol, Carbomer, Polysorbate 20, Palmitoyl Oligopeptide and Palmitoyl Tetrapeptide 7, for instance available as Mathxyl 3000 from Sederma Inc.

According to the invention skin conditioning agents are cosmetic ingredients which help to maintain the soft, smooth and pliable appearance of the skin and can also act as humactants, emollients or occlusives. Skin conditioning agents help to strengthen the skins barrier function and act by attracting and holding moisture in the skin.

Suitable skin conditioning agents, are vitamins, mineral salts, trace elements, plant extracts, animal extracts, proteins or enzymes, natural and/or synthetic oils, and/or fats. Suitable skin conditioning agents are known to the skilled person. Examples are allantoin, L-carnitine, extracts of plants of the genus aloe, preferably aloe vera, aloe barbadensis or aloe andongensis, chamomile essence, ceramides, cholesterol, phenyl trimethicone or compounds containing polyethylene glycol and/or polypropylene glycol. Preferred skin conditioning agents according to the invention are natural and/or synthetic oils and/or fats.

Every natural or synthetic oil which is used in the personal care/cosmetic industry is suitable for the cosmetic basic composition according to the invention. In particular, saturated and/or unsaturated vegetable oils, for instance nut oils, such as *Aleurites Moluccana* nut oil, brazil nut oil, groundnut oil, hazel nut oil, macadamia nut oil, peanut oil, apricot oil, avocado oil, borage oil, butyl stearate, $C_{12}$-$C_{15}$ alkyl benzoates, $C_{10}$-$C_{20}$ chain triglycerides, cacao butter, calendula oil, castor oil, cetyl alcohols, cetyl palmitate, coconut oil, cotton seed oil, evening primrose oil, grape seed oil, jojoba oil, mango butter, medium chain ($C_6$ to $C_{12}$) triglycerides (MCTs), mineral oil, mink oil, olive oil, palm kernel oil, rapeseed oil, retinal oil, ricinus oil, safflower oil, sesame oil, shea butter, soy bean oil, spermaceti oil, St. John's wort oil, sun flower oil, sweet almond oil, sweet corn oil, thistle oil or wheat germ oil and mixtures thereof are preferably used. In a preferred embodiment the oil phase of the cosmetic basic composition of the invention comprises at least safflower oil (INCI: *Carthamus Tinctorius* (safflower) seed oil), sun flower oil (*Helianthus Annuus* (sun flower) seed oil) or a mixture thereof. Suitable oils are for instance available under the trade names organic sunflower oil (e.g. Desert Whale), or EMCON sun-Org (e.g. The Fanning Corporation) and certified organic safflower oil (F1-Sciences).

According to the invention emollients can be added to prevent water lost and to soften and smoothen the skin. Suitable emollients are for instance silicones, such as cyclomethicone or dimethicone, hydrocarbons, fatty alcohols, synthetic and natural oils, petrolatum based emollients, such as petroleum jelly or lanolin. Other suitable emollients are known by the skilled person.

UV-filter can be added to the cosmetic basic composition of the invention to protect the skin from UVA and UVB radiation. Suitable oil soluble UVB-filters are 4-aminobenzoic acid and derivatives thereof, such as octyl dimethyl para-aminobezoic acid or 4-dimethylaminobenzoic acid-2-ethylhexyl ester, cinnamic acid and derivatives thereof, such as octyl p-methoxycinnamate or 4-methoxycinnamic acid-2-ethylhexyl ester, benzophenones and derivatives thereof, such as 2-hydroxy-4-methoxybenzophenone or benzophenone-3, 3-benzylidene camphor and derivatives thereof, such as methylbenzylidene camphor, butyl methoxybenzoyl methane, octyl salicylate, or homosalate and mixtures thereof. Suitable water soluble UVB-filters are sulfonic acid derivatives of benzophenone or 3-benzylidene camphor or salts thereof, such as sodium or potassium of 2-phenylbenzimidazole-5-sulfonic acid.

Suitable UVA-filters are dibenzoylmethane and derivatives thereof, such as 1-phenyl-4-(4'-isopropylphenyl)propane-1,3-dione, butyl methoxybenzoylmethane or menthyl anthranilate or mixtures thereof. According to the invention broad bandpass filter can also be used, such as derivatives of bis-resorcinyltriazine or benzoaxoles.

In a preferred embodiment of the invention the at least one cosmetically active substance contained in the Oleosomes is a mixture of tocopherol and a vegetable oil, preferably safflower oil. The content of the antioxidant tocopherol is in the range of 40 mg to 80 mg per 100 g Oleosomes, preferably at about 60 mg per 100 g Oleosomes. In another preferred embodiment of the invention natural Oleosomes of *Carthamus Tinctorius* are used which are not loaded with further ingredients. In another preferred embodiment of the invention natural Oleosomes of *Carthamus Tinctorius* are used which are not loaded with further oil soluble ingredients as shown above.

According to the invention the Oleosomes are contained in an amount of 0.1 to 30 percent by weight, preferably in an amount of 1 to 20 percent by weight and most preferred in an amount of 5 to 15 percent by weight based on the total weight of the cosmetic basic composition.

In a preferred embodiment of the invention water is contained in the cosmetic basic composition in an amount of 50 to 95 percent by weight, preferably in an amount of 60 to 80 percent by weight, most preferred in an amount of 65 to 80 and more preferred in an amount of 65 to 70 percent by weight based on the total weight of the cosmetic basic composition. Due to the high water content the cosmetic basic composition of the invention shows moisturizing properties and hydrates the skin during wearing.

Advantageously the texture of the cosmetic basic composition of the invention remains constant over a broad pH range. In particular the viscosity does not change with a change in pH. Further, cosmetically active ingredients are released very constantly over time from the composition.

In another preferred embodiment of the invention the cosmetic basic composition may comprise additional cosmetically active substances, preferably anti-oxidants, anti-aging agents, anti-wrinkles agents, sun protectants, cooling actives or insects repellents or mixtures thereof. If present, said additional active substances are not included into the Oleosomes but are formulated separately into the aqueous or oily phase of the emulsion. If present, the additional active ingredients are contained in an amount of 0.1 to 5 weight percent, preferably in an amount of 0.1 to 2 weight percent based on the total weight of the cosmetic basic composition.

As additional formulated antioxidants, anti-aging agents, anti-wrinkles agents or sun-protectants all substances can be used which are also contained in the Oleosomes. As insect repellent, plant extracts, such as citric oil, orange oil, melissa oil, eucalyptus oil, lavender oil or pink oil or diethyl toluamide or mixtures thereof are used. Suitable other insect repellents are known to the skilled person.

To impart a fresh and comfortable feeling to the skin cooling actives may be formulated into the cosmetic basic composition of the invention. Suitable cooling actives according to the invention can be menthol and its derivatives, for instance menthyl lactate (FRESCOLAT ML) or menthone glycerin acetal (FRESCOLAT MGA).

In a preferred embodiment the cosmetic basic composition comprises cosmetically acceptable auxiliary substances, preferably skin conditioning agents, humectants, emollients, wetting agents, natural or synthetic oils, colorants, powders, fillers, opacifying agents, preservatives, flavoring agents or fragrance ingredients or mixtures thereof. Up to 2 percent by weight of flavoring agents or fragrances can be contained in the cosmetic basic composition of the invention based on the total weight of the cosmetic basic composition.

As skin conditioning agents, emollients and natural or synthetic oils are all substances that can be used which also may be contained in the Oleosomes. According to the invention skin conditioning agents, emollients or natural or synthetic oils (with the exception of silicone oils) may be contained in an amount of 0.1 to 10 percent by weight, preferably 0.1 to 7.5 percent by weight, more preferred at about 5 percent by weight based on the total weight of the cosmetic basic composition.

In a preferred embodiment humectants or wetting agents may be contained in the basic composition.

Suitable humectants are known to the skilled person. Examples for wetting agents are glycerin and derivatives thereof, for instance polyglycehn 10, decaglyceryl decaoleate sorbitan trioleate, polyglycerol-3-diisostearate, sorbitan sesquioleate, glycerol triisostearate, diethanolamine or lecithin. In a preferred embodiment the cosmetic basic composition of the invention contains lecithin as a wetting agent, for example Emulmetik 100 (e.g. available from Lukas Meyer, Germany). Further suitable wetting agents are known to the skilled person. According to the invention wetting agents are preferably contained in an amount of 0.1 to 5 percent by weight, more preferred 0.1 to 2 percent by weight based on the total weight of the cosmetic basic composition.

In a further preferred embodiment of the invention the cosmetic basic composition further comprises preservatives to stabilize the composition over time.

Suitable preservatives are for instance parabens, phenoxyethanol, caprylyl glycol, sorbic acid, glucono delta lactone, sodium benzoate or any typical preservative or mixtures thereof used in the personal care/cosmetic industry. In a preferred embodiment a mixture of sorbic acid (6 weight percent), caprylyl glycol (41.0 weight percent) and phenoxyethanol (53.0 weight percent), available for instance as Optiphen Plus e.g. from ISP Corp. Up to 2 percent by weight of preservatives may be contained in the cosmetic basic composition of the invention based on the total weight of the cosmetic basic composition.

In a preferred embodiment the cosmetic basic composition of the invention contains 0.1 to 10 percent by weight, preferably 0.1 to 7.5 percent by weight, more preferred 0.1 to 5 percent by weight of cosmetically acceptable auxiliary substances based on the total weight of the cosmetic basic composition.

In a preferred embodiment the cosmetic basic composition of the invention also comprises colorants. As a colorant cosmetically acceptable pigments, natural or synthetic organic dyes or natural or synthetic inorganic dyes and mixtures thereof may be used. According to the invention pigments may be white or colored, mineral or organic particles that are insoluble in the solvent and which are intended to color and/or opacify the composition. Examples for mineral pigments which can be used according to the invention are for instance titanium oxide, titanium dioxide, zirconium oxide or cerium oxide, and also zinc oxide, iron (II; III) oxide, such as, Brown Iron Oxide C33-115, Yellow Iron Oxide CG 450, Yellow Iron Oxide C33-1700, Red Iron Oxide C33-2199 or Black Iron Oxide C33-5000, chromium oxide, such as Chrome Oxide Green CG 525, bismuth oxychloride or their mixtures. Further, ferric blue, manganese violet, copper powder and bronze powder may be used. As organic pigments the use of carbon black, and barium, strontium, calcium (D & C Red No. 7) and aluminium lakes is preferred. Dyes may be soluble in the aqueous or the oily phase of the emulsion. Further suitable dyes are for example Red 7 Ca. Lake, Sudan red, D & C Red 17, D & C Green 6, beta-carotene, soybean oil, Sudan brown, D & C Yellow 11, D & C Violet 2, D & C Orange 5, quinoline yellow, annatto and beetroot juice. According to the invention mineral pigments, in particular titanium dioxide, Yellow Iron Oxide C33-1700, Red Iron Oxide C33-2199 or Black Iron Oxide C33-5000 and mixtures thereof are preferred.

In another preferred embodiment nacres or goniochromatic pigments, for example multilayer interference pigments, and/or reflective pigments may be included into the cosmetic basic composition. As nacres coated mica can be used according to the invention. The mica can be coated with titanium oxide, iron oxide, natural pigments or bismuth oxychloride.

The colorants are present in an amount sufficient to impart a color to the human skin on which it is applied. The composition of the invention includes at about 0.1 to about 30 weight % colorants, preferably at about 0.5 to about 25 weight %, more preferred at about 1 to about 20 weight % and most preferred at about 5 to about 15 weight %. All weight % are based on the total weight of the cosmetic basic composition.

Cosmetically acceptable fillers are known by the skilled person. Suitable fillers are for example mineral silicates, such as mica and talc, starch, kaolin, nylon, zinc oxide, titanium oxide, precipitated calcium carbonate or synthetic polymer powders, such as acrylate powders, for instance polymethylmetacrylate (PMMA) powders and combinations thereof. According to the invention mineral silicate fillers, in particular mica and talc are preferred. If included, fillers are contained in the cosmetic basic composition of the invention in an amount of 0.1 to 10 percent by weight, preferably in an amount of 1 to 5 percent by weight based on the total weight of the cosmetic basic composition.

In a preferred embodiment of the invention the cosmetic basic composition comprises flavouring agents or fragrance ingredients to improve the odor of the cosmetic product.

Cosmetically acceptable flavouring agents and fragrances are known to the skilled person. In one embodiment of the invention natural fragrances, such as plant and fruit extract or essences are preferred.

Preferred examples of cosmetic products which comprise the cosmetic basic composition of the invention are skin care cosmetics and foundations. Skin care cosmetics according to the invention comprise the hydroxypropylmethylcellulose $C_{15}$-$C_{20}$ alkyl ether thickener, Oleosomes, water, at least one skin conditioning agent and optionally, anti-aging agents, wetting, agents, humactants, fragrances and preservatives. Foundations according to the invention comprise the hydroxypropylmethylcellulose $C_{15}$-$C_{20}$ alkyl ether thickener, Oleosomes, water, at least one colorant, and optionally skin conditioning agents, wetting agents, humactants, fragrances and preservatives.

The present invention further relates to the use of the cosmetic basic composition of the invention for skin care or skin protection in products of decorative cosmetics or personal care cosmetics. The cosmetic basic composition of the invention is preferably used (in the preparation of) lotions, emulsions, creams, gels or flexible solids. The cosmetic basic composition of the invention is preferably used for skin care or skin protection of sensitive skin.

Examples for personal care products according to the invention are skin care cosmetics, moisturizing preparations, ointments, cleansers, make-up removers, night and day treatments, skin reparatives and sunscreens, or every other cosmetic product which should repair, moisturize, smooth, condition, protect, clean and rejuvenate the skin or prevent the loss of moisture and reverse damages of the skin. Examples for products of decorative cosmetic are color foundations, make-ups, concealing sticks, rouge, tanning creams, eye shadow creams or every other cosmetic product which should color or lighten the skin.

In general the cosmetic basic composition of the invention can be used to impart the special properties of the cosmetic basic composition, in particular long wearing properties, transfer resistance or moisturizing properties or a mixture of these properties to a cosmetic product.

In a further object the present invention provides a method of preparing the cosmetic basic composition of the invention comprising adding water and Oleosomes into a main kettle and stirring the mixture at 800 rpm at room temperature, optionally premixing cosmetically acceptable auxiliary substances and/or additional cosmetically active substances and adding the premix to the main kettle under stirring at 1200 rpm at room temperature, slowly adding the hydroxypropylmethylcellulose $C_{15}$-$C_{20}$ alkyl ether thickener to the main kettle under stirring at 2500 rpm at room temperature, increasing the stirring speed to at least 3000 rpm as soon as the mixture begins to thicken and stirring until an uniform gel is formed. Optionally further cosmetically acceptable auxiliary substances and/or additional cosmetically active substances may be added consecutively to the gel under continuous stirring until a good and stable dispersion is achieved.

According to the invention the cosmetic basic composition is prepared by mixing the Oleosomes and water under stirring at 800 rpm at room temperature and slowly adding the hydroxypropylmethylcellulose-dehvative thickener to the main kettle under stirring at 2500 rpm at room temperature. Then the stirring speed is increased to at least 3000 rpm as soon as the mixture begins to thicken and stirred until an uniform gel is formed. The resulting cosmetic basic composition of the invention shows self-levelling properties.

In a preferred embodiment of the preparation method of the invention the initial mixture of Oleosomes and water is stirred for at least 10 min. Preferably soluble cosmetically acceptable auxiliary substances and/or additional cosmetically active substances, more preferred skin conditioning agent(s), wetting agent(s) and/or anti-aging agent(s) are added to the initial mixture of Oleosomes and water. After adding the mixture is stirred for at least another 10 min. After the addition of the hydroxypropylmethylcellulose $C_{15}$-$C_{20}$ alkyl ether thickener the viscosity of the mixture increases and the mixture is stirred by at least 3000 rpm for at least 30 min. As soon as an uniform gel is formed stirring is stopped and the cosmetic basic composition of the invention is achieved. If further cosmetically acceptable auxiliary substances and/or additional cosmetically active substances are added said substance are added one by one. After the addition of every substance the gel is stirred for at least 30 min until a good dispersion is achieved. Preferably colorant(s) or filler(s) are added according to the invention. Preservatives and fragrances can be added last at moderate stirring.

The cosmetic basic composition of the invention shall be exemplified by the following examples.

Example 1: Foundation

| | |
|---|---|
| 0.1-2.0 weight % | Hydroxypropylmethylcellulose Ci5-C2o alkyl ether thickener |
| 5.0-15.0 weight % | Oleosomes |
| 60.0-80.0 weight % | Water |
| 0.1-7.5 weight % | Skin conditioning agent(s) |
| 0.1-2.0 weight % | Wetting agent(s) |
| 0.1-15.0 weight % | Colorant(s) 0.1-5.0 weight % Filler(s) |
| 0.1-2.0 weight % | Preservative(s) |
| 0.0-2.0 weight % | Fragrance(s) |

The foundation of Example 1 is prepared as shown below. Water and Oleosomes are added into a main kettle and the mixture is stirred for 10 min at room temperature using a Sylverson stirrer at 800 rpm. The skin conditioning agent(s) and the wetting agent(s) are premixed in a separate kettle and the premix is added to the main kettle and stirred at 1200 rpm for 10 to 15 min at room temperature. Then the hydroxypropylmethylcellulose $C_{15}$-$C_{20}$ alkyl ether thickener is added slowly to the main kettle and stirred at 2500 rpm at room temperature. As the mixture begins to thicken the stirrer speed is increased to 3000-3200 rpm and the mixture is stirred for additional 30 minutes or until an uniform gel is formed. Then the colorant(s) are added one by one to main kettle at room temperature. The gel is stirred at 3500-4000 rpm for 30 min to ensure a good dispersion between each addition. The glass sides are checked for pigment dispersion. If the pigment is still not dispersed the gel is stirred for another 10 min to ensure a satisfactory dispersion. After the colorant(s) the filler(s) are added using the same procedure as for the colorant(s). Finally preservatives and optionally fragrances are added to the gel. Stirring at 300 rpm is sufficient to dissolve preservatives and fragrances homogeneously in the gel.

Example 2: Foundation

| Weight % | INCI-name | Trade name |
|---|---|---|
| 0.50 | Hydroxypropylmethylcellulose Stearoxy Ether | Sangelose 9OL |

-continued

| Weight % | INCI-name | Trade name |
|---|---|---|
| 10.00 | *Carthamus Tinctorius* (Safflower) Oleosomes | Hydresia |
| 67.25 | Water | Water |
| 5.00 | Organic sunflower Oil | EMCON sun-Org |
| 0.50 | Lecithin | Emulmetik 100 |
| 9.54 | TiO$_2$ | TiO$_2$ C47-056 |
| 1.63 | Yellow Oxide | Yellow C33-1700 |
| 0.55 | Red Oxide | Red C33-2199 |
| 0.28 | Black Oxide | Black C33-5000 |
| 2.50 | Mica | Silk mica |
| 1.50 | Mica | Sericite GMS-4C |
| 0.75 | Sorbic acid & Caprylyl glycol & Phenoxyethanol | Optiphen plus |

The foundation of Example 2 is prepared according to Example 1. Hydresia and water were premixed as well as EMCON sun-org and Emulmetik 100. The latter mixture was added to the mixture of Hydresia and water under stirring as shown above. The gel was formed by adding the Sangelose 90L according to Example 1. Color oxides were added one by one as well as the mica. Optiphen plus is added last as preservative.

Example 3: Skin Care Cosmetics

| | | |
|---|---|---|
| 0.1-2.0 weight % | Hydroxypropylmethylcellulose C$_{15}$-C$_{20}$ alkyl ether thickener | |
| 5.0-15.0 weight % | Oleosomes | |
| 60.0-80.0 weight % | Water 0.1-7.5 weight % Skin conditioning agent(s) | |
| 0.1-2.0 weight % | Wetting agent(s) | |
| 0.1-7.5 weight % | Anti-aging agent(s) | |
| 0.1-2.0 weight % | Preservative(s) | |
| 0.0-2.0 weight % | Fragrance(s) | |

Skin care cosmetics of Example 3 are prepared according to Example 1. Skin conditioning agent(s), wetting agent(s) and anti-aging agent(s) are premixed and added to the mixture of Oleosomes and water prepared as shown in Example 1. The gel is formed by slowly adding the hydroxypropylmethylcellulose Ci5-C2o alkyl ether thickener as shown above. Preservatives and optionally fragrances are added last under moderate stirring.

Example 4: Skin Care Cosmetics

| Weight % | INCI-name | Trade name |
|---|---|---|
| 0.50 | Hydroxypropylmethylcellulose Stearoxy Ether | Sangelose 90L |
| 10.00 | *Carthamus Tinctorius* (Safflower) Oleosomes | Hydresia |
| 78.25 | Water | Water |
| 5.00 | Organic sunflower Oil | EMCON sun-Org |
| 0.50 | Lecithin | Emulmetik 100 |
| 5.00 | Glycerin - Water - Butylene Glycol - Carbomer - Polysorbate 20 - Palmitoyl Oligopeptide - Palmitoyl Tetrapeptide 7 | Matrixyl 3000 |
| 0.75 | Sorbic acid & Caprylyl glycol & Phenoxyethanol | Optiphen plus |

Matrixyl 3000 (item code: SE26770) is a mixture comprising at about 25% water, at about 20% Butylene Glycol, at about 1% Carbomer, at about 0.5% Polysorbate 20, at about 100 ppm Palmitoyl Oligopeptide, at about 50 ppm Palmitoyl Tetrapeptide 7 and the remainder Glycerin.

Skin care cosmetics of example 4 were prepared according to Example 1. Hydresia and water were premixed as well as EMCON sun-org, Emulmetik 100 and Matrixyl 3000. The latter mixture was added to the mixture of Hydresia and water under stirring as shown in Example 1. The gel was formed by adding the Sangelose 90L according to Example 1. Optiphen plus is added last as preservative.

Example 5: Storage Stability

To determine the storage stability of the cosmetic basic composition of the invention the foundation of Example 2 was stored by constant temperature and alternate temperature cycles for two months. As temperatures 25° C., 37° C. and 45° C. were used, respectively. For alternate temperature cycles temperature was changed every 24 hours. In addition, stability was also checked by alternating freezing and thawing of the foundation for two months. The stability of the emulsion was checked every week.

After two months changes in the texture, the stability of the emulsion or other properties of the cosmetic basic composition were not observed. Thus, the cosmetic basic composition of the present invention shows a high storage stability.

As a further stability parameter the viscosity of the foundation stored at 25° C. was also measured. Viscosity was measured over 24 hours using a spindle viscosimeter. Spindle TC-speed was 10 rpm, measuring time was 1 min and measurement was repeated every week. Viscosity of the foundation was at about 31000 cps. Changes in viscosity were not observed over two months.

Example 6: Comparative Tests

For comparative tests the cosmetic basic composition of the invention was prepared as a foundation according to Example 2 comprising 0.5 weight % hydroxypropylmethylcellulose stearoxy ether (Sangelose 90L) as thickener according to the invention. Instead of Sangelose 90L alternative cellulose thickeners were tested. As alternative cellulose thickeners hydroxypropyl methyl-cellulose (Methocel) or hydroxyethylcellulose (Natrosol) (0.5 weight %, each) were used in the foundation of Example 2.

Using the alternative cellulose thickeners Methocel and Natrosol stable emulsions could not be achieved. The foundations separated directly into two phases. Thus, only the special combination of ingredients according to the invention results in the stable cosmetic basic composition of the invention showing the excellent cosmetic properties as shown below in the consumer tests.

Example 7: Consumers Tests

The foundation of Example 2 based on the cosmetic basic composition of the invention was used for a monadic consumer study. Thirty female panelists, ranging in age from 20 to 63 years were selected for this study. All panelists were in good health and are regular users of foundations. The foundation of Example 2 was applied once a day for one week. During the study the panelists did not used other foundation products. The foundation was evaluated with respect to common cosmetic properties such as wearing comfort or application and the special properties, long lasting, transfer resistance and moisturizing.

The texture and the overall application of the foundation was evaluated "good" or better by more than 60% of the consumers and more than 80% felt the product is lightweight and comfortable to wear all day. Easy blending was confirmed by more than 70% of the panelists. Thus a cosmetic product was provided which meet the common requirements of the consumers.

Nearly all panelists (93%) confirmed that the foundation is long lasting, wherein more than 70% felt that the foundation last longer than 9 hours, nearly 50% felt that the foundation last longer than 11 hours and at least 20% confirmed that the foundation last longer than 15 hours. In addition the foundation shows a high transfer resistance (confirmed by more than 60%) and hydrating and moisturizing properties (about 60%).

Thus the cosmetic basic composition of the invention provides a very special combination of cosmetic properties.

As the consumer study was performed with a foundation also the concealing properties of the product were evaluated. 60% to 70% of the panelists confirmed that the foundation hide imperfections, minimizes the appearance of fine lines and wrinkles and conceals dark eye circles. Thereby, it was shown that the special cosmetic properties of the cosmetic basic composition of the invention do not influence other cosmetic functions.

What is claimed:

1. A cosmetic basic composition comprising:
   0.50 weight % Hydroxypropylmethylcellulose Stearoxy Ether
   10.00 weight % *Carthamus Tinctorius* (Safflower) Oleosomes
   67.25 weight % Water
   5.00 weight % Organic sunflower Oil
   0.50 weight % Lecithin
   9.54 weight % $TiO_2$
   1.63 weight % Yellow Oxide
   0.55 weight % Red Oxide
   0.28 weight % Black Oxide
   4.00 weight % Mica
   0.75 weight % Sorbic acid & Caprylyl glycol & Phenoxyethanol
   wherein the Oleosomes comprise an antioxidant,
   and wherein all indications in percent by weight refer to percent by weight based on the total weight of the composition.

2. The cosmetic basic composition of claim 1, wherein the antioxidant is Vitamin E.

3. A cosmetic basic composition comprising:
   0.50 weight % Hydroxypropylmethylcellulose Stearoxy Ether
   10.00 weight % *Carthamus Tinctorius* (Safflower) Oleosomes
   78.25 weight % Water
   5.00 weight % Organic sunflower Oil
   0.50 weight % Lecithin
   5.00 weight % Glycerin—Water—Butylene Glycol—Carbomer Polysorbate 20—Palmitoyl Oligopeptide—Palmitoyl Tetrapeptide 7
   0.75 Sorbic acid & Caprylyl glycol & Phenoxyethanol
   wherein the Oleosomes comprise an antioxidant,
   and wherein all indications in percent by weight refer to percent by weight based on the total weight of the composition.

4. The cosmetic basic composition of claim 3, wherein the antioxidant is Vitamin E.

* * * * *